United States Patent

Morishita

[11] Patent Number: 5,962,702
[45] Date of Patent: Oct. 5, 1999

[54] PROCESS FOR PRODUCTION OF TRIOXANE

[75] Inventor: Hirohisa Morishita, Kurashiki, Japan

[73] Assignee: Asahi Kasei Kogyo Kabushiki Kaisha, Osaka, Japan

[21] Appl. No.: 08/809,410

[22] PCT Filed: Oct. 24, 1995

[86] PCT No.: PCT/JP95/02179

§ 371 Date: Apr. 24, 1997

§ 102(e) Date: Apr. 24, 1997

[87] PCT Pub. No.: WO96/13496

PCT Pub. Date: May 9, 1996

[30] Foreign Application Priority Data

Oct. 27, 1994 [JP] Japan ................................. 6-286155

[51] Int. Cl.$^6$ .................. C07D 323/06; C07D 323/04
[52] U.S. Cl. .......................................... 549/368; 549/367
[58] Field of Search ..................................... 549/367, 368

[56] References Cited

U.S. PATENT DOCUMENTS 4,967,014  10/1990  Masamoto et al. ..................... 568/458

FOREIGN PATENT DOCUMENTS

| 1 526 132 | 4/1968 | France . |
| 55-164680 | 12/1980 | Japan . |
| 59-134789 | 8/1984 | Japan . |
| 59-134789 | 12/1984 | Japan . |
| 1 020 812 | 2/1966 | United Kingdom . |
| 1 171 715 | 11/1969 | United Kingdom . |

OTHER PUBLICATIONS

European Search Report for European Application No. EP 95934875.6, Dec. 1995, p. 1–2.

Chemical Abstracts, 1993, vol. 118, No.25, p. 892.

Chemical Abstracts, 1991, vol. 115, No. 28, p. 947

*Primary Examiner*—Johann Richter
*Assistant Examiner*—Dominic Keating
*Attorney, Agent, or Firm*—Pennie & Edmonds LLP

[57] ABSTRACT

A process for producing trioxane by contacting an aqueous formaldehyde solution comprising 67 wt. % formaldehyde, 30 wt. % water and 3 wt. % methanol with an acidic catalyst comprising a cation exchange resin containing a sulfonic acid group. The concentration of methanol, and formic acid which is generated during the reaction, are both controlled between 0.5–5.0 wt. % and the concentration of methanol in terms of wt. % is controlled so as not to exceed two times the concentration of formic acid in terms of wt. %. With this process, the amounts of by-products formed are small, and trioxane can be produced efficiently.

9 Claims, No Drawings

PROCESS FOR PRODUCTION OF TRIOXANE

TECHNICAL FIELD

The present invention relates to a process for producing trioxane by cyclizing formaldehyde to convert it into a cyclic trimer. More particularly, the present invention relates to a process for producing trioxane by contacting an aqueous formaldehyde solution with an acidic catalyst, wherein the concentrations of methanol and formic acid present in the reaction system are each controlled and wherein the amounts of by-products formed are small.

BACKGROUND ART

Trioxane has been produced by cyclizing formaldehyde in its aqueous solution in the presence of an acidic catalyst such as sulfuric acid, cation exchange resin having a sulfonic acid group, zeolite or the like.

These conventional processes for trioxane production have not been satisfactory because of various problems such as corrosion of production equipment, precipitation of paraformaldehyde at high formaldehyde concentration, low trioxane selectivity and the like. For example, when a sulfuric acid catalyst is used, there is a problem of equipment corrosion by strong acid and it is necessary to use an expensive material(s) for equipment to prevent the problem. When a cation exchange resin having a sulfonic acid group is used as a catalyst, there are problems such as low trioxane selectivity, paraformaldehyde precipitation and consequent pressure loss of catalyst layer, and the like. Meanwhile, it is well known that increased methanol concentration in reaction system is effective for the prevention of paraformaldehyde precipitation in aqueous formaldehyde solution. Increased methanol concentration in reaction system, however, invites formation of larger amounts of by-products such as methyl formate, dioxymethylene dimethoxide, trioxymethylene dimethoxide and the like, which is undesirable. JP-A-59-134789 discloses that trioxane selectivity is higher when a macroreticular cation exchange resin having a sulfonic acid group is used and the concentration of formic acid is controlled at 0.025–15.0 wt. %. The concentration of formic acid in this literature, however, refers to a formic acid concentration in raw materials mixture fed into reactor, i.e. a formic acid concentration before start of reaction and is not a formic acid concentration in reaction system during reaction. Incidentally, too high a formic acid concentration causes equipment corrosion by formic acid.

DISCLOSURE OF INVENTION

The present invention is intended to provide a process for producing trioxane by contacting an aqueous formaldehyde solution with an acidic catalyst, wherein the corrosion of equipment material(s) is very low, the amounts of by-products formed are small, and trioxane can be produced efficiently.

In order to solve the above-mentioned problems of the prior art, the present inventors eagerly made a study. As a result, the present inventors surprisingly found out a process for production of trioxane wherein the equipment corrosion is prevented and the amounts of by-products formed, i.e. dioxymethylene dimethoxide and trioxymethylene dimethoxide are reduced by controlling the methanol concentration and formic acid concentration in the reaction system and the concentration ratio of methanol to formic acid in synthesis of trioxane in the presence of an acidic catalyst. The finding has led to the completion of the present invention.

The present invention provides a process for producing trioxane by contacting an aqueous formaldehyde solution with an acidic catalyst, wherein the concentrations of methanol and formic acid present in the reaction system are controlled each at 0.5–5 wt. % and the concentration of methanol in terms of wt. % is controlled so as not to exceed two times the concentration of formic acid in terms of wt. %.

BEST MODE FOR CARRYING OUT THE INVENTION

In the present invention, an aqueous formaldehyde solution is used as a raw material. The formaldehyde concentration in said solution is generally 30–80 wt. %, preferably 60–75 wt. %. The aqueous formaldehyde solution as raw material may contain methanol, methylal, formic acid, methyl formate, trioxane, etc.

The acidic catalyst used in the present invention is preferably a cation exchange resin having a sulfonic acid group, more preferably a macroreticular cation exchange resin having a sulfonic acid group. The macroreticular cation exchange resin is a resin called under the name of MR type, porous type or the like, and has a large number of fine pores of several tens to several thousands Å, preferably 250–1,400 Å in diameter, a surface area of 10–150 m$^2$/g and a porosity of 0.15–1.0 ml/ml. The contact of the aqueous formaldehyde solution with the cation exchange resin can be conducted by various methods, for example, a method of passing an aqueous formaldehyde solution through a fixed or fluidized bed packed with a cation exchange resin to contact the solution with the bed, or a method of suspending a cation exchange resin in an aqueous formaldehyde solution.

The feeding of the aqueous formaldehyde solution as raw material, into its reaction system can be conducted, for example, by feeding the aqueous formaldehyde solution directly into a reactor, or by first feeding the raw material into a distillation tower to concentrate the raw material therein and then contacting the raw material concentrate with a catalyst at the bottom of the distillation tower, or taking out the raw material concentrate from the bottom to contact with a catalyst. The formaldehyde concentration in the reaction system is preferably 55–80 wt. %, more preferably 60–75 wt. %, in view of the production efficiency of trioxane and the precipitation of paraformaldehyde, etc.

One important point of the present invention is the concentrations of methanol and formic acid present in the reaction system. Such methanol and formic acid includes not only those contained in the aqueous formaldehyde solution fed as a raw material but also those formed as by-products during the reaction. It is necessary that the concentrations of methanol and formic acid present in the reaction system during reaction be controlled each at 0.5–5.0 wt. % and, preferably, the methanol concentration be controlled at 0.5–3.0 wt. % and the formic acid concentration be controlled at 0.5–5.0 wt. %. When the methanol concentration is less than 0.5 wt. %, paraformaldehyde precipitates easily and, as a result, it is difficult to conduct the intended reaction at a high formaldehyde concentration and it is also difficult to keep low the formic acid concentration in the reaction system, which tends to invite corrosion of production equipment. When the methanol concentration is more than 5 wt. %, the total amount of dioxymethylene dimethoxide and trioxymethylene dimethoxide formed is large. In order to control the formic acid concentration lower than 0.5 wt. %, it is necessary to make the reaction temperature low and the catalyst amount small; at such a low temperature and at such a small catalyst amount, an efficient synthesis of trioxane is difficult.

Another important point of the present invention is the ratio of methanol concentration to formic acid concentration in reaction system. In the present invention, the methanol concentration is controlled so as not to exceed two times the formic acid concentration. By controlling the concentration ratio of methanol to formic acid in this range, it is possible to sufficiently suppress the formation of by-products, i.e. dioxymethylene dimethoxide and trioxymethylene dimethoxide.

The control of methanol concentration and concentration ratio of methanol to formic acid in reaction system can be made, for example, by changing the methanol concentration in the feed, i.e. an aqueous formaldehyde solution fed or by, when the feed is fed into a distillation tower, changing the very tray(s) into which the feed is fed. The reaction temperature can be set between 60° C. and 125° C. Too low a reaction temperature incurs paraformaldehyde precipitation, and too high a reaction temperature invites a reduced selectivity and deteriorated quality of catalyst used.

An example of the mode for carrying out the present invention in industry, is shown below.

An aqueous formaldehyde solution as raw material is fed into two points of a distillation tower, i.e. one point of the intermediate trays and one point of the lower trays; thereby, the methanol and formic acid concentrations in reaction system are controlled each in the above-mentioned range; the bottom solution in distillation tower is circulated through a cation exchange resin-filled reactor and a reboiler; thus, trioxane is synthesized at a given temperature. The synthesized trioxane is distilled from the distillation tower top together with water, formaldehyde and by-products; then, the distillate is contacted with an organic solvent to extract trioxane into the organic solvent; the organic solvent phase after extraction is subjected to a purification step to obtain trioxane of high purity.

The present invention is hereinafter described in more detail by Examples and Comparative Examples.

EXAMPLE 1 (PRESENT INVENTION)

An aqueous formaldehyde solution 1 as raw material 1 consisting of 65 wt. % of formaldehyde, 3 wt. % of methanol and the remainder of water was fed into an intermediate tray (15th tray) of a distillation tower having 30 bubble cap trays. An aqueous formaldehyde solution 2 as raw material 2 having the same composition as the raw material 1 was fed into the bottom of the distillation tower. They were fed at a weight ratio of the raw material 1/the raw material 2 being 8/2. In a circulation line for tower bottom solution was provided a fixed catalyst bed, a reaction layer, filled with 10 l of a cation exchange resin (Amberlite 200C, a product of Organo Co.), and the bottom solution was circulated through the circulation line at a rate of 500 l/hr. While the total feed rate of the raw material formaldehyde solutions were being controlled to keep the bottom solution at a given level, the bottom solution was heated by a heater to conduct synthesis of trioxane; distillation was conducted at a reflux ratio of 2.0 to take out a distillate at a rate of 10 kg/hr, and trioxane was obtained. The bottom solution and the distillate were analyzed by gas chromatography to measure their compositions. In the circulation line of the bottom was provided a SUS 304 test piece, and its corrosion after continuous 10-day operation was examined visually.

The results are shown in Table 1. There was neither precipitation of paraformaldehyde nor corrosion of test piece, and the total amount of dioxymethylene dimethoxide and trioxymethylene dimethoxide formed as by-products was 0.77 wt. % based on formed trioxane.

EXAMPLES 2–5 (PRESENT INVENTION) AND EXAMPLES 6–9 (COMPARISON)

Using the same apparatus as in Example 1, trioxane was synthesized in various cases by changing the methanol concentration in the aqueous formaldehyde solution of raw materials 1 and 2 or the feed rate ratio of raw materials 1 and 2 to change the composition of the bottom solution. The results are shown in Table 1. In each of the Examples according to the present invention, there was neither precipitation of paraformaldehyde nor corrosion of test piece, and the total amount of dioxymethylene dimethoxide and trioxymethylene dimethoxide formed as by-products was 1 wt. % or less based on formed trioxane. In contrast, as seen in Example 6 (comparison) or Example 9 (comparison), when the methanol concentration in reaction system exceeded 5 wt. % or two times the formic acid concentration, the total amount of dioxymethylene dimethoxide and trioxymethylene dimethoxide formed was large; as seen in Example 7 (comparison), when the methanol concentration in reaction system was less than 0.5 wt. %, paraformaldehyde precipitated in the reaction system; as seen in Example 8 (comparison), when the formic acid concentration in reaction system exceeded 5 wt. %, there was test piece corrosion.

TABLE 1

| No. | Raw material Composition (wt. %) | Example 1 (present invention) | Example 2 (present invention) | Example 3 (present invention) | Example 4 (present invention) | Example 5 (present invention) |
|---|---|---|---|---|---|---|
| 1 | Formaldehyde | 67 | 67 | 67 | 67 | — |
|   | Water | 30 | 30 | 30 | 29 | — |
|   | Methanol | 3 | 3 | 3 | 4 | — |
| 2 | Formaldehyde | 67 | 67 | 67 | — | 67 |
|   | Water | 30 | 30 | 30 | — | 29 |
|   | Methanol | 3 | 3 | 3 | — | 4 |
| Raw material 1/raw material 2 | | 4 | 9 | 0.5 | ∞ | 4 |
| Bottom solution composition (wt. %) | | | | | | |
| Formaldehyde | | 69.8 | 70.5 | 68.6 | 71.0 | 68.2 |
| Water | | 20.0 | 19.0 | 22.1 | 18.2 | 21.7 |

TABLE 1-continued

|  | | | | | |
|---|---|---|---|---|---|
| Methanol | 1.8 | 0.8 | 2.8 | 0.7 | 3.4 |
| Formic acid | 3.2 | 4.2 | 2.0 | 4.6 | 1.9 |
| Distillate composition (wt. %) | | | | | |
| TOX | 48.2 | 48.6 | 46.2 | 46.9 | 46.0 |
| DOM | 0.28 | 0.21 | 0.30 | 0.20 | 0.32 |
| tom | 0.06 | 0.03 | 0.06 | 0.02 | 0.08 |
| (DOM + TOM)/TOX[%] | 0.71 | 0.49 | 0.78 | 0.47 | 0.87 |
| Corrosion of test piece (SUS 304) | No | No | No | No | No |
| Paraformaldehyde precipitation in bottom solution | No | No | No | No | No |

|  |  | Example 6 (comparison) | Example 7 (comparison) | Example 8 (comparison) | Example 9 (comparison) |
|---|---|---|---|---|---|
| No. | Raw material Composition (wt. %) | | | | |
| 1 | Formaldehyde | — | 67 | 67 | — |
|  | Water | — | 30 | 30 | — |
|  | Methanol | — | 3 | 3 | — |
| 2 | Formaldehyde | 67 | — | 67 | 67 |
|  | Water | 26 | — | 30 | 30 |
|  | Methanol | 7 | — | 3 | 3 |
| Raw material 1/raw material 2 | | 0 | ∞ | 0.5 | 0 |
| Bottom solution composition (wt. %) | | | | | |
| Formaldehyde | | 68.1 | 71.0 | 68.2 | 68.1 |
| Water | | 19.5 | 19.5 | 17.2 | 22.3 |
| Methanol | | 6.5 | 0.3 | 2.8 | 2.7 |
| Formic acid | | 1.1 | 4.5 | 7.5 | 1.1 |
| Distillate composition (wt. %) | | | | | |
| TOX | | 45.6 | 46.0 | 46.4 | 46.0 |
| DOM | | 2.05 | 0.16 | 0.21 | 1.24 |
| tom | | 0.33 | 0.02 | 0.03 | 0.25 |
| (DOM + TOM)/TOX[%] | | 5.22 | 0.39 | 0.52 | 3.24 |
| Corrosion of test piece (SUS 304) | | No | Paraformaldehyde precipitation acid consequent difficulty of long-term operation | Yes | No |
| Paraformaldehyde precipitation in bottom solution | | No | Yes | No | No |

Raw material 1: fed into the 15th tray,
Raw material 2: fed into a circulation line for the tower bottom.
TOX: trioxane,
DOM: dioxymethylene dimethoxide,
TOM: trioxymethylene dimethoxide

I claim:

1. A process for producing trioxane comprising the step of contacting an aqueous solution comprising formaldehyde and methanol with an acid catalyst, a total concentration of methanol in the aqueous solution being no greater than 5 wt. %, wherein
    the concentrations of methanol and formic acid produced during the process are controlled each at 0.5–5 wt. % and the concentration of methanol in terms of wt. % is controlled so as not to exceed two times the concentration of formic acid in terms of wt. %.

2. The process according to claim 1, wherein the acidic catalyst is a cation exchange resin containing a sulfonic acid group.

3. The process according to claim 1, wherein the concentration of formaldehyde present in the aqueous solution is 60–75 wt. %.

4. A process for producing trioxane comprising the steps of:
    contacting an aqueous solution comprising formaldehyde and methanol with an acid catalyst, a total concentration of methanol in the aqueous solution being no greater than 5 wt. %, and
    controlling concentrations of both methanol, and formic acid which is produced during the process, at 0.5–5 wt. % with the wt. % of methanol not exceeding two times the wt. % of formic acid.

5. A process for producing trioxane comprising the step of contacting an aqueous formaldehyde solution with an acid catalyst, wherein the concentrations of any methanol and formic acid present during the process are controlled each at 0.5–5 wt. % and the concentration of methanol in terms of wt. % is controlled so as not to exceed two tines the concentration of formic acid in terms of wt. %.

6. The process according to claim 5, wherein the acidic catalyst is a cation exchange resin containing a sulfonic acid group.

7. The process according to claim 5, wherein the concentration of formaldehyde present in the aqueous solution is 60–75 wt. %.

8. The process according to claim 5, wherein said aqueous formaldehyde solution also includes, as an initial raw material, one from the group consisting of methanol, methylal, formic acid, methyl formate and trioxane, and mixtures thereof.

9. The process according to claim 8, wherein said aqueous formaldehyde solution includes methanol.

* * * * *